United States Patent [19]
Michelotti et al.

[11] Patent Number: 5,866,513
[45] Date of Patent: Feb. 2, 1999

[54] ARYL-SUBSTITUTED CYCLOALKANES AND CYCLOALKENES AND HERBICIDAL USE THEREOF

[75] Inventors: Enrique Luis Michelotti, Ft. Washington; Renee Caroline Roemmele, Maple Glen, both of Pa.; Colin Swithenbank, Worton, Md.; Colin Michael Tice, Elkins Park; David Hamilton Young, Ambler, both of Pa.

[73] Assignee: Rohm and Haas Company, Philadelphia, Pa.

[21] Appl. No.: 805,545

[22] Filed: Feb. 25, 1997

Related U.S. Application Data

[60] Provisional application No. 60/005,270 Oct. 12, 1995.

[51] Int. Cl.$^6$ ................................................. A01N 31/08
[52] U.S. Cl. ......................... 504/309; 504/310; 504/351; 504/355
[58] Field of Search .................................. 504/309, 310, 504/351, 355

[56] References Cited

FOREIGN PATENT DOCUMENTS

| 0 090 516 | 5/1983 | European Pat. Off. . |
| 0 090 526 | 5/1983 | European Pat. Off. . |

OTHER PUBLICATIONS

Chemical Abstracts, vol. 120, No. 1, Jan. 3, 1994, Columbus, Ohio, U.S., abstract No. 008229.
Chemical Abstracts, vol. 61, No. 12, 1964, Columbus, Ohio, U.S., abstract No. 14728g.
Chemical Abstracts, vol. 48, No. 5, 1954, Columbus, Ohio, U.S., abstract No. 3272g.
Journal of the American Chemical Society, vol. 75, 1953, DC US, pp. 4852–4853.
Journal of Pharmaceutical Sciences, vol. 54, No. 10, 1965, Washington US, pp. 1552–1553.
Journal of Organic Chemistry, vol. 17, 1952, Easton US, pp. 581–594.
Journal of Organic Chemistry, vol. 26, 1961, Easton US, pp. 5220–5221.
Journal of the Chemical Society, 1951, Letchworth GB, pp. 2524–2529.
Berichte Der Deutschen Chemischen Gesellschaft, vol. 72, 1939, Weinheim, DE, pp. 675–678 (English translation or equivalent will follow in the mail).
Bryce, M.R.; Gardiner, J.M., *Tetrahedron* 44L2, p. 599 (1988).
Wildman, W.C.; Wildman, R.B., Journal of Organic Chemistry, 17, 581 (1952).
Lloyd, H.A.; Kielar, E.A.; Highet, R.J., Uyeo, S., Fabs, H.M.; Wildman, W.C., Journal of Organic Chemistry, 27, 373 (1962).
Barltrop, J.A.; Nicholson, J.S., Journal of the Chemical Society, 1951, p. 2524.

*Primary Examiner*—Brian M. Burn
*Attorney, Agent, or Firm*—Thomas D. Rogerson

[57] ABSTRACT

Disclosed are herbicidal aryl substituted cycloalkyl and aryl substituted cycloalkenyl compounds, herbicidal compositions, and herbicidal use of the compounds and compositions. The aryl substituent is selected from substituted phenyl, unsubstituted or substituted five-membered heterocycle, and unsubstituted or substituted six-membered heterocycle.

11 Claims, No Drawings

ARYL-SUBSTITUTED CYCLOALKANES AND CYCLOALKENES AND HERBICIDAL USE THEREOF

This is a provisional application Ser. No. 60/005270 filed Oct. 12, 1995.

This invention relates to the use of a class of aryl substituted cycloalkanes and aryl substituted cycloalkenes and compositions thereof as selective herbicides which are effective against both monocot and dicot weed species in either preemergence or postemergence applications. This invention also provides new aryl substituted cycloalkanes and cycloalkenes as well as methods of preparing these compounds.

Aryl substituted cyclohexanes and cyclohexenes with plant growth regulating activity are disclosed in *Agrokhimiya* 1975, (6), 116–22 and *Fitogorn. Rost Rast.* 1978, 82–90. The disclosed compounds act as seedling growth stimulants. There is no suggestion that such compounds are herbicidal. *Tetrahedron,* 44(2), 599 (1988) and *J. Org. Chem.,* 17, 581 (1952) report the use of aryl substituted nitrocyclohexenes as intermediates in the synthesis of alkaloids and cyclohexanones and cyclohexenones. Again, there is no suggestion that such compounds are herbicidal.

We have discovered a class of aryl substituted cycloalkanes and aryl substituted cycloalkenes which, rather than acting as plant growth stimulants, act as selective herbicides. Although a wide variety of herbicidal compounds and compositions are known for the control of unwanted vegetation, the need continues for novel and improved herbicidal compounds and compositions. This is particularly true for situations wherein a crop is infested with botanically similar weeds, for example, when a crop such as corn is infested with grassy weeds. In addition, weeds can become resistant to known herbicides over time. To overcome such resistance, economic and environmental considerations often favor herbicides having different modes of action than those currently used.

This invention provides a method of controlling unwanted vegetation comprising contacting the unwanted vegetation with an herbicidally effective amount of a compound of the following general formula I:

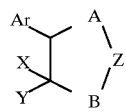

wherein:

Ar is selected from phenyl substituted with from 2 to 5 substituents, naphthyl substituted with from 2 to 7 substituents, five-membered aromatic heterocycle unsubstituted or substituted with from 1 to 3 substituents, and six-membered aromatic heterocycle unsubstituted or substituted with from 1 to 4 substituents wherein the five or six-membered heterocycle contains from 1 to 3 heteroatoms independently selected from O, S, and N and the phenyl, naphthyl, and heterocycle substituents are independently selected from halo; cyano; nitro; hydroxy; mercapto; thiocyanato; alkyl; alkoxy; haloalkyl; haloalkoxy; alkenylthio; alkynylthio; alkylthio; alkenylsulfinyl; alkenylsulfonyl; alkynylsulfinyl; alkynylsulfonyl; alkylsulfinyl; haloalkylthio; haloalkylsulfinyl; haloalkylsulfonyl; alkylthiocarbonyl; alkoxythiocarbonyl; aminothiocarbonyl; alkylaminothiocarbonyl; dialkylaminothiocarbonyl; alkylsulfonyl; carboxy; formyl; alkylcarbonyl; alkoxycarbonyl; alkanoyloxy; amino; alkylamino; dialkylamino; carbamoyl; alkylcarbamoyl; dialkylcarbamoyl; cyanoalkyl; alkoxyalkyl; alkenyl; alkadienyl; alkynyl; alkyldithionate; alkylcarbonylthio; trialkylsilyl; unsubstituted or substituted phenyl, phenoxy, benzoyl, phenoxycarbonyl, phenylthio, phenylalkyl wherein the substituents are independently selected from one to two of the group consisting of halo, cyano, nitro, hydroxy, alkyl, alkoxy, haloalkyl, haloalkoxy, alkylthio, alkylsulfinyl, alkylsulfonyl, carboxy, formyl, alkylcarbonyl, alkoxycarbonyl, alkanoyloxy, amino, alkylamino, and dialkylamino; or when two adjacent positions on a phenyl, naphthyl, or heterocyclic ring are substituted with alkoxy, alkylthio, alkylsulfinyl or alkylsulfonyl groups these groups may be joined to form a 5 or 6 membered heterocyclic ring;

A and B are independently selected from CR, CRR$^a$, and NR$^1$;

Z is selected from CR, CRR$^a$, CRR$^a$—CR$^b$R$^c$, CH$_2$—CR=CR$^d$, CR=CR$^d$, NR$^1$, S, SO, SO$_2$, O, N=N, and CR=N, with the appropriate single and double bonds between A, B, and Z;

R$^1$ is independently selected from H and alkyl;

R, R$^a$, R$^b$, and R$^c$ are independently selected from H, alkyl, hydroxyl, alkoxy, haloalkyl, haloalkoxy, carboxyl, formyl, alkylcarbonyl, alkoxycarbonyl, alkenylthio; alkynylthio; alkylthio; alkenylsulfinyl; alkenylsulfonyl; alkynylsulfinyl; alkynylsulfonyl; alkylsulfinyl; alkylsulfonyl; haloalkylthio; haloalkylsulfinyl; haloalkylsulfonyl; halogen, cyano, nitro, amino, alkylamino, dialkylamino, aminocarbonyl, alkylaminocarbonyl, alkylcarbonylamino, and dialkylaminocarbonyl;

R$^d$ is selected from H, alkyl, alkoxy, haloalkyl, haloalkoxy, carboxyl, formyl, alkylcarbonyl, alkoxycarbonyl, alkenylthio; alkynylthio; alkylthio; alkenylsulfinyl; alkenylsulfonyl; alkynylsulfinyl; alkynylsulfonyl; alkylsulfinyl; alkylsulfonyl; haloalkylthio; haloalkylsulfinyl; haloalkylsulfonyl; halogen, cyano, nitro, amino, alkylamino, dialkylamino, aminocarbonyl, alkylaminocarbonyl, and dialkylaminocarbonyl;

X and Y are independently selected from H, NO$_2$, CN, halogen, alkyl, alkylcarbonylamino, alkoxycarbonyl, formyl, alkylcarbonyl, haloalkyl, dialkylphosphonate, alkylphosphinate, alkylphosphonamido, dialkylphosphonamido, trialkylphosphonamido, tetraalkylphosphonamido, aminocarbonyl, alkylaminocarbonyl, dialkylaminocarbonyl, oximino, alkyloximino, dialkylhydrazone, provided that X and Y are not both H or both alkyl;

its salts, diastereomers, and stereoisomers.

Unless otherwise specified, the term "alkyl" means a (C$_1$–C$_6$) straight chain alkyl group, a (C$_3$–C$_6$) branched chain alkyl group, or a (C$_3$–C$_6$) cycloalkyl group. Preferred alkyl groups are the (C$_1$–C$_4$) straight chain, the (C$_3$–C$_4$) branched chain, and the (C$_3$–C$_6$) cyclo alkyls. The terms "alkenyl" and "alkynyl" mean a (C$_1$–C$_6$) alkyl containing one or more carbon-carbon double or triple bonds, respectively. Preferred are the (C$_2$–C$_4$) alkenyl and (C$_2$–C$_4$) alkynyl groups. The term "alkoxy" means an alkyl, alkenyl, or alkynyl group attached to the remainder of the compound through an oxygen linkage. The term "aromatic heterocycle" means an aromatic heterocyclic ring containing two or more carbon atoms and one or more heteroatoms independently selected from O, N, and S. Examples of five- and six-membered aromatic heterocycles include 2 and 3-thienyl; 2 and 3-furyl; 1, 2, and 3-pyrrolyl; 2, 3, and 4-pyridyl; 3 and 4-pyridazinyl; 2, 4, and 5-pyrimidinyl; and 2-pyrazinyl.

Because of their high activity and selectivity, preferred compounds are those of formula I wherein Ar is a disubstituted or trisubstituted phenyl, wherein the substituents are selected from halo, $(C_1-C_4)$alkyl, $(C_1-C_4)$alkoxy, cyano, halo$(C_1-C_4)$alkyl, A and B are both $CH_2$, one of X and Y is selected from H, $(C_1-C_4)$alkyl, and halo and the other of X and Y is selected from $NO_2$, CN, $(C_1-C_4)$alkyloximino, $(C_1-C_4)$dialkylhydrazone and aminocarbonyl, and Z is selected from $CH_2$—$CH_2$ and CH=CH.

Because of their outstanding herbicidal activity and selectivity the most preferred compounds of formula I are those wherein Ar is 2,3,4-trisubstituted phenyl, wherein the substituents are selected from $(C_1-C_4)$alkyl, $(C_1-C_4)$alkoxy, and halo, A and B are both $CH_2$, one of X and Y is H and the other of X and Y is selected from $NO_2$ and CN, and Z is selected from $CH_2$—$CH_2$ and CH=CH.

In another embodiment, this invention provides compounds of formula I, as defined in the above-described method, but with the proviso that when one of X and Y is $NO_2$, and the other of X and Y is H, and Z is CH=CH then Ar is other than 3-methoxyphenyl, 2,4-dimethoxyphenyl, 3,4-dimethoxyphenyl, 3,4,5-trimethoxyphenyl, and 3,4-methylenedioxyphenyl, which are useful as herbicides. A third aspect of this invention relates to herbicidal compositions comprising one or more compounds of formula I and an agronomically acceptable carrier.

The term "contacting" means applying one or more compounds of formula I or a composition comprising one or more compounds of formula I and an agronomically acceptable carrier to unwanted vegetation, to the locus of the unwanted vegetation, or to the growth medium of the unwanted vegetation.

Some embodiments of this invention are described in detail in the following examples.

Table I lists representative example compounds. Table II provides nuclear magnetic resonance data for a number of the examples listed in Table I.

TABLE I

Structures of Prepared Examples

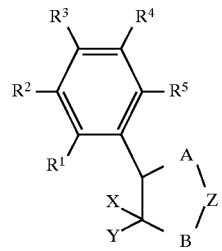

| Ex # | R1 | R2 | R3 | R4 | R5 | A | Z | B | X | Y | mp °C. |
|------|------|------|------|------|----|-----|---------|-----|--------|-------|--------|
| 1 | H | OMe | OMe | H | H | CH2 | CH=CH | CH2 | NO2 | H | NMR |
| 2 | H | OMe | OMe | H | H | CH2 | CH2—CH2 | CH2 | NO2 | H | NMR |
| 3 | H | Me | OMe | H | H | CH2 | CH=CH | CH2 | NO2 | H | NMR |
| 4 | H | Me | OMe | H | H | CH2 | CH2—CH2 | CH2 | NO2 | H | NMR |
| 5 | H | H | OMe | H | H | CH2 | CH=CH | CH2 | NO2 | H | NMR |
| 6 | H | OMe | H | H | H | CH2 | CH=CH | CH2 | NO2 | H | NMR |
| 7 | H | H | Me | H | H | CH2 | CH=CH | CH2 | CH2NO2 | H | NMR |
| 8 | H | —CH=CH—CH=CH— | H | H | H | CH2 | CH=CH | CH2 | NO2 | H | NMR |
| 9 | Br | H | OMe | OMe | H | CH2 | CH=CH | CH2 | NO2 | H | NMR |
| 10 | OMe | OMe | OMe | H | H | CH2 | CH=CH | CH2 | CN | CN | 78–80° |
| 11 | H | OMe | OMe | H | H | CH2 | CMe=CMe | CH2 | NO2 | H | NMR |
| 12 | OMe | OMe | OMe | H | H | CH2 | CH=CH | CH2 | NO2 | H | NMR |
| 13 | OMe | OMe | OMe | H | H | CH2 | CH=CH | CH2 | CN | CO2Et | 96–97° |
| 14 | H | OCH2O | H | H | H | CH2 | CH=CH | CH2 | NO2 | H | NMR |
| 15 | H | Cl | Cl | H | H | CH2 | CH=CH | CH2 | NO2 | H | NMR |
| 16 | H | Br | OMe | OMe | H | CH2 | CH=CH | CH2 | NO2 | H | NMR |
| 17 | H | F | OMe | H | H | CH2 | CH=CH | CH2 | NO2 | H | NMR |
| 18 | OMe | OMe | OMe | H | H | CH2 | CH2—CH2 | CH2 | NO2 | H | NMR |
| 19 | Cl | H | O— | OCH2 | H | CH2 | CH=CH | CH2 | NO2 | H | NMR |
| 20 | H | OMe | H | OMe | H | CH2 | CH=CH | CH2 | NO2 | H | NMR |
| 21 | OMe | H | OMe | H | H | CH2 | CH=CH | CH2 | NO2 | H | NMR |
| 22 | Me | Me | OMe | H | H | CH2 | CH=CH | CH2 | NO2 | H | NMR |
| 23 | OMe | Me | OMe | H | H | CH2 | CH=CH | CH2 | NO2 | H | NMR |
| 24 | NO2 | OMe | OMe | H | H | CH2 | CH=CH | CH2 | NO2 | H | NMR |
| 25 | H | Cl | H | Cl | H | CH2 | CH=CH | CH2 | NO2 | H | NMR |
| 26 | H | Cl | OMe | H | H | CH2 | CH=CH | CH2 | NO2 | H | NMR |
| 27 | OMe | OMe | H | H | H | CH2 | CH=CH | CH2 | NO2 | H | NMR |
| 28 | H | OMe | OMe | OMe | H | CH2 | CH=CH | CH2 | NO2 | H | NMR |
| 29 | Cl | OMe | OMe | H | H | CH2 | CH=CH | CH2 | NO2 | H | NMR |
| 30 | H | H | CF3 | H | H | CH2 | CH=CH | CH2 | NO2 | H | NMR |
| 31 | H | H | CN | H | H | CH2 | CH=CH | CH2 | NO2 | H | NMR |
| 32 | OEt | OMe | OMe | H | H | CH2 | CH=CH | CH2 | NO2 | H | NMR |
| 33 | OiPr | OMe | OMe | H | H | CH2 | CH=CH | CH2 | NO2 | H | NMR |

TABLE I-continued

Structures of Prepared Examples

| Ex # | R1 | R2 | R3 | R4 | R5 | A | Z | B | X | Y | mp °C. |
|------|-----|-----|-----|----|----|-----|-----|-----|-----|-----|-----|
| 34 | OnBu | OMe | OMe | H | H | CH2 | CH=CH | CH2 | NO2 | H | NMR |
| 35 | OMe | OMe | OMe | H | H | CH2 | CMe=CH, CH=CMe (mixture) | CH2 | NO2 | H | NMR |
| 36 | OMe | OMe | OMe | H | H | CH2 | CH2—CH2 | CH2 | Me2N—N= | | NMR |
| 37 | OMe | OMe | OMe | H | H | CH2 | CH2—CH2 | CH2 | MeN= | | NMR |
| 38 | OMe | OMe | OMe | H | H | NMe | O | CH2 | NO2 | H | NMR |
| 39 | OMe | OMe | OMe | H | H | CH= | CH.CH2 | CH2 | H | NO2 | 75–90° |
| 40 | OMe | OMe | OMe | H | H | CH2 | CH2—CH2 | CH | NO2 | H | 73–75° |
| 41 | OMe | OMe | OMe | H | H | CH2 | CH2—CH2 | CH2 | CONH2 | H | 45–48° |
| 42 | OMe | OMe | OMe | H | H | CH2 | CH2—CH2 | CH2 | CN | H | 69–70° |
| 43 | OMe | OMe | OMe | H | H | CH2 | CH=CH | CH2 | NO2 | H | 134–136° |
| 44 | OMe | OMe | OMe | H | H | CH2 | CH=CH | CH2 | NO2 Br | Br NO2 | NMR |
| 45 | OMe | OMe | OMe | H | H | CH2 | CH2 | CH2 | NO2 H | H NO2 | NMR |
| 46 | H | H | H | H | H | CH2 | CH=CMe, CMe=CH (mixture) | CH2 | NO2 | H | NMR |
| 47 | OEt | OEt | OEt | H | H | CH2 | CH=CH | CH2 | NO2 | H | 76–78° |
| 48 | Me | Me | Me | H | H | CH2 | CH=CH | CH2 | NO2 | H | 68–70° |
| 49 | OMe | Et | OMe | H | H | CH2 | CH=CH | CH2 | NO2 | H | NMR |
| 50 | Cl | Cl | Cl | H | H | CH2 | CH=CH | CH2 | NO2 | H | 82–85° |
| 51 | Et | OMe | OMe | H | H | CH2 | CH=CH | CH2 | NO2 | H | NMR |
| 52 | OMe | OMe | OMe | H | H | CH2 | CH=CH | CH2 | CN | CO2H | 120° (dec.) |
| 53 | OMe | OMe | OMe | H | H | CH2 | CH=CH | CH2 | CN (T/C mix) | H | NMR |
| 54 | OMe | OMe | OMe | H | H | CH2 | CH=CH | CHCH3 | NO2 | H | NMR |
| 55 | OMe | OMe | OMe | H | H | CH2 | CH=CH | CH2 | NO2 | CH3 | NMR |
| 56 | OMe | OMe | OMe | H | H | CH2 | CH=CH | CHOCH3 | NO2 | H | 81–83 |
| 57 | OMe | OMe | OMe | H | H | CHOCH3 | CH=CH | CH2 | NO2 | H | 114–116 |
| 58 | OMe | OMe | OMe | H | H | CH(CH2) bonded to B | CH=CH | CH bonded to A | NO2 | H | NMR |
| 59 | OMe | OMe | OMe | H | H | CH(CH2)2 bonded to B | CH=CH | CH bonded to A | NO2 | H | 82–86 |
| 60 | OMe | OMe | OMe | H | H | CH2 | CH=CCH3 | CH2 | NO2 | H | 80–84 |
| 61 | OMe | OMe | OMe | H | H | C(CH3) | CH=CH | C(CH3) | NO2 | H | NMR |
| 62 | OMe | OMe | OMe | H | H | CH2 | C(CH3)=C(CH3) | CH2 | NO2 | H | 113–114 |
| 63 | OMe | OMe | OMe | H | H | CH2 | (CH2)3 | CH2 | NO2 | double bond between phenyl and CX | NMR |

TABLE 1A

Ar—A—Z  
 \\B  
X—Y

| Ex # | Aryl | A | Z | B | X | Y | mp °C. |
|---|---|---|---|---|---|---|---|
| 64 | 6-methoxy-3-pyridyl | CH2 | CH=CH | CH2 | NO2 | H | 49–50 |
| 65 | 6-methoxy-5-methyl-2-pyridyl | CH2 | CH=CH | CH2 | NO2 | H | oil |
| 66 | 6-methoxy-5-methyl-3-pyridyl | CH2 | CH=CH | CH2 | NO2 | H | 129–131 |
| 67 | 4-chloro-1-methyl-3-pyrazolyl | CH2 | CH=CH | CH2 | NO2 | H | 100–102 |
| 68 | 3-thienyl | CH2 | CH=CH | CH2 | NO2 | H | 50–52 |
| 69 | 2-thienyl | CH2 | CH=CH | CH2 | NO2 | H | 70–72 |
| 70 | 4-methyl-2-thienyl | CH2 | CH=CH | CH2 | NO2 | H | oil |
| 71 | 2-bromo-4-methyl-3-thienyl | CH2 | CH=CH | CH2 | NO2 | H | 107–108 |
| 72 | 5-methyl-3-thienyl | CH2 | CH=CH | CH2 | NO2 | H | oil |
| 73 | 3-methoxy-2-thienyl | CH2 | CH=CH | CH2 | NO2 | H | 73–75 |
| 74 | 4-chloro-2-thienyl | CH2 | CH=CH | CH2 | NO2 | H | 95–97 |
| 75 | 2,3-dichloro-4-thienyl | CH2 | CH=CH | CH2 | NO2 | H | 97–98 |
| 76 | 2,5-dichloro-3-thienyl | CH2 | CH=CH | CH2 | NO2 | H | 106–107 |

TABLE II

Nuclear Magnetic Resonance Data

| Ex. # | $^1$H NMR (260MHz, CDCl$_3$ Unless otherwise specified) |
|---|---|
| 1 | (d$_6$-DMSO) 2.3–2.9 (m, 4H), 3.1–3.4 (m, 1H), 3.70 (s, 3H), 3.75 (s, 3H), 5.1–5.3 (m, 1H), 5.6–5.9 (m, 2H), 6.75–7.0 (m, 3H). |
| 2 | 1.4–2.5 (m, 8H), 3.0–3.2 (m, 1H), 3.8 (s, 3H), 3.9 (s, 3H), 4.5–4.7 (m, 1H), 6.65–6.85 (m, 3H) |
| 3 | 2.18 (s, 3H), 2.2–2.9 (m, 4H), 3.2–3.4 (m, 1H), 3.78 (s, 3H), 4.8–5.0 (m, 1H), 5.65–5.9 (m, 2H), 6.75 (d, 1H), 6.98 (s, 1H), 7.0 (d, 1H). |
| 4 | 2.15 (s, 3H), 1.2–2.5 (m, 8H), 2.9–3.15 (m, 1H), 3.78 (s, 3H), 4.5–4.75 (m, 1H), 6.72 (d, 1H), 6.95. (s, 1H), 6.98 (d, 1H). |
| 5 | 2.2–2.9 (m, 4H), 3.7–3.9 (m, 1H), 3.75 (s, 3H), 4.75–4.98 (m, 1H), 6.6–6.85 (m, 2H), 6.82 (d, 2H), 7.12 (d, 2H). |
| 6 | 2.2–3.0 (m, 4H), 3.3–3.5 (m, 1H), 3.8 (s, 3H), 4.9–5.1 (m, 1H), 5.7–5.9 (m, 2H), 6.7–7.3 (m, 4H). |
| 7 | 2.3 (s, 3H), 2.2–2.85 (m, 4H), 3.3–3.5, (m, 1H), 4.8–5.0 (m, 1H), 5.65–5.9 (m, 2H), 7.25 (d, 1H), 7.45 (d, 1H). |
| 8 | 2.3–3.0 (m, 4H), 3.5–3.7 (m, 1H); 4.95–5.2 (m, 1H), 5.65–5.95 (m, 2H), 7.2–8.0 (m, 7H). |
| 9 | 2.1–2.9, (m,, 4H), 3.9–4.1 (m, 1H), 3.9 (s, 3H), 3.95 (s, 3H), 5.0–5.2 (m, 1H), 5.7–5.9. (m, 2H), 6.75 (s, 1H), 7.0 (s, 1H). |
| 11 | 1.7 (s, 3H), 1.8 (s, 3H), 2.0–3.0 (m, 4H), 3.25–3.5 (m, 1H), 3.75 (s, 3H), 3.8 (s, 3H), 4.75–5.0 (m, 1H), 6.6–6.9 (m, 3H). |
| 12 | 2.1–2.9 (m, 4H), 3.6–3.9 (m, 1H), 3.85 (s, 3H), 3.90 (s, 3H), 3.,95 (s, 3H), 5.0–5.2 (m, 1H), 5.6–5.9 (m, 2H), 6.6 (d, 2H), 6.9 (d, 2H). |
| 14 | 2.1–2.9 (m.4H), 3.2–3.5 (m, 1H), 4.8–5.0 (m, 1,H), 5.6–5.9 (m, 1H), 6.9 (s, 2H), 6.6–6.9 (m, 3H). |
| 15 | 2.1–2.9 (m, 4H), 3.3–3.5, (m, 1H), 4.8–5.0 (m, 1H), 5.6–5.9 (m, 2H), 7.0–7.5 (m, 3H), |
| 16 | 2.1–2.9 (m, 4H), 3.2–3.4 (m, 1H), 3.8 (s, 3H), 3.85 (s, 3H), 4.8–5.0 (m, 1H), 5.6–5.9 (m, 1H), 6.7 (s, 1H), 7.0 (s, 1H). |
| 17 | 2.1–2.9 (m, 4H), 3.2–3.5 (m, 1H), 3.9 (s, 3H), 4.8–5.0 (m, 1H), 5.6–5.9 (m, 2H), 6.8–7.1 (m, 3H). |
| 18 | 1.4–2.5 (m, 8H), 3.3–3.6 (m, 1H), 3.8 (s, 3H), 3.85 (s, 3H), 3.9 (s, 3H), 4.8–5.0 (m, 1H), 6.6 (d, 1H), 6.85 (d, 1H). |
| 19 | 2.0–3.0 (m, 4H), 3.9–4.1 (m, 1H), 4.9–5.2 (m, 1H), 5.6–5.9 (m, 2H), 6.0 (s, 2H), 6.75 (s, 1H), 6.85 (s, 1H). |
| 20 | 2.2–2.9 (m, 4H), 3.3–3.5 (m, 1H), 3.8 (s, 6H), 4.9–5.1 (m, 1H), 5.6–5.9 (m, 2H), 6.35 (s, 1H), 6.4 (s, 2H). |
| 21 | 2.0–2.9 (m, 4H), 3.5–3.8 (m, 1H), 3.85 (s, 6H), 5.2–5.4 (m, 1H), 5.6–5.9 (m, 1H), 6.4 (d, 1H), 6.45 (s, 1H), 7.05 (d, 1H). |
| 22 | 2.2 (s, 3H), 2.3 (s, 3H), 2.0–2.9 (m, 4H), 3.6–3.9 (m, 1H), 3.8 (s, 3H), 4.9–5.2 (m, 1H), 5.6–6.0 (m, 2H), 6.75 (d, 1H), 7.05 (d, 1H). |
| 23 | 2.15 (s, 3H), 2.0–2.9 (m, 4H), 3.5–3.9 (m, 1H), 3.75 (s, 3H), 3.8 (s, 3H), 5.0–5.2 (m, 1H), 5.6–5.9 (m, 2H), 6.65 (d, 1H), 7.05 (d, 1H) |
| 24 | 2.1–2.9 (m, 4H), 3.3–3.5 (m, 1H), 3.85 (s, 3H), 3.9 (s, 3H), 4.9–5.1 (m, 1H), 5.6–5.9 (m, 1H), 6.9–7.1 (m, 2H). |
| 25 | 2.1–2.9 (m, 4H), 3.3–3.5 (m ,1H), 4.8–5.0 (m, 1H), 5.6–5.9 (m, 2H), 7.15 (s, 2H), 7.25 (s, 1H). |

TABLE II-continued

Nuclear Magnetic Resonance Data

| Ex. # | $^1$H NMR (260MHz, CDCl$_3$ Unless otherwise specified) |
|---|---|
| 26 | 2.1–2.9 (m, 4H), 3.3–3.5 (m, 1H), 3.85 (s, 3H), 4.8–5.0 (m, 1H), 5.6–5.9 (m, 2H), 6.85 (d, 1H), 7.1 (dd, 1H), 7.25 (d, 1H). |
| 27 | 2.1–2.9 (m, 4H), 3.8–3.9 (m, 1H), 3.85 (s, 3H), 3.9 (s, 3H), 5.05–5.25 (m, 1H), 5.6–5.9 (m, 2H), 6.75–7.1 (m, 3H). |
| 28 | 2.1–2.9 (m, 4H), 3.3–3.5 (m, 1H), 3.8 (s, 3H), 3.85 (s, 6H), 4.9–5.1 (m, 1H), 5.6–5.9 (m, 2H), 6.45 (s, 2H). |
| 29 | 2.6–2.9 (m, 4H), 3.85 (s, 6H), 3.8–4.1 (m, 1H), 5.0.–5.2 (m, 1H), 5.6–5.9 (m, 2H), 6.85 (d, 1H), 7.0 (d, 1H). |
| 30 | 2.0–2.9 (m, 4H), 3.4–3.6 (m, 1H), 4.9–5.1 (m, 1H), 5.6–5.9 (m, 2H), 7.4 (d, 2H), 7.6 (d, 2H). |
| 31 | 2.1–2.9 (m, 4H), 3.4–3.6 (m, 1H), 4.9–5.1 (m, 1H), 5.6–5.9 (m, 2H), 7.4 (d, 2H), 7.65 (d, 2H). |
| 32 | 2.1–2.9 (m, 4H), 3.7–3.9 (m, 1H), 3.8 (s, 3H), 3.85 (s, 3H), 4.0–4.3 (m, 1H), 5.0–5.2 (m, 1H), 5.6–5.9 (m, 2H), 6.6(d, 2H), 6.85 (d, 2H). |
| 33 | 0.8–1.0 (m, 6H), 2.1–2.9 (m, 4H), 3.8 (s, 3H), 3.85 (s, 3H), 3.8–4.0 (m, 1H), 4.7–4.9 (m, 1H), 5.0–5.2 (m, 1H), 5.6–5.9 (m, 2H), 6.6 (d, 2H), 6.9 (d, 2H). |
| 34 | 0.8–1.0 (m, 3H), 1.0–1.7 (m, 2H), 2.1–2.9 (m, 4H), 3.8 (s, 3H), 3.85 (s, 3H), 3.7–4.0 (m, 1H), 4.0–4.2 (m, 2H), 5.0–5.2 (m, 1H), 5.6–5.9 (m, 2H), 6.6 (d, 1H), 6.9 (d, 1H). |
| 35 | 2.1–2.9 (m, 4H), 3.7–4.0 (m, 1H), 3.8 (s, 3H), 3.85 (s, 3H), 3.95 (s, 3H), 5.0–5.2 (m, 1H), 5.4–5.6 (m, 1H), 6.65 (d, 1H), 6.85 (d, 1H). |
| 36 | 1.4–2.6(8H), 2.35 (s, 6H), 3.1 (1H, m, 1H), 3.8 (s, 9H), 6.65 (d, 1H), 6.9 (d, 1H). |
| 37 | (major isomer) 1.4–2.1 (8H), 3.2 (m, 1H), 3.65 (s, 3H), 3.85 (s, 6H), 6.65 (d, 1H), 6.9 (d, 1H). |
| 37 | (minor isomer) 1.4–2.6 (8H), 3.2 (m, 1H), 3.75 (s, 3H), 3.9 (s, 6H), 6.6 (d, 1H), 6.8 (d, 1H). |
| 38 | 2.7 (s, 3H), 3.85 (s, 6H), 3.9 (s, 3H), 4.3 (dd, 1H), 4.35 (d, 1H), 4.5 (dd, 1H), 5.35 (m, 1H), 6.7 (d, 1H), 7.05 (d, 1H). |
| 44 | 2.3–3.7 (4H), 3.8 (s, 6H), 3.9 (s, 3H), 4.5 (m, 1H), 5.8 (m, 1H), 5.95 (m, 1H), 7.0 (d, 1H). |
| 45 | 1.7–2.5 (m, 6H), 3.7–4.1 (m, 10h), 5.0 (m, 0.5H), 5.3 (m, 0.5H), 6.6 (d, 0.5H), 6.65 (d, 0.5H), 6.85 (d, 0.5H), 6.90 (d, 0.5H). |
| 46 | (d$_6$-acetone) d 1.8 (s, 3H), 2.4 (d, b, 2H), 2.9 (t, b, 2H), 3.5 (m, 1H), 5.2 (m, 1H), 5.5 (s, b, 1H), 7.2–7.7 (m, 5H). |
| 49 | 1.2 (t, 3H), 2.2–2.4 (m, 2H), 2.7 (q, 2H), 2.9 (m, 2H), 3.8 (ds, 6H), 3.8 (m, 1H), 5.1 (m, 1H), 5.8 (m, b, 2H), 6.6 (d, 1H), 7.0 (d, 1H). |
| 51 | 1.2 (t, 3H), 2.2–2.6 (m, 2H), 2.7–2.9 (m, b, 4H), 3.6 (m, 1H), 3.8 (ds, 6H), 5.0 (m, 1H), 5.8 (m, b, 2H), 6.7 (d, 1H), 6.9 (d, 1H). |
| 53 | mix of isomers 2.1–2.8 (m, 4H), 3.1 (m, 1H), 3.4 (m, 1H), 3.8–4.0 (m, 9H), 5.7–6.0 (m, 2H), 6.7 (m, 1H), 6.9 (d, 0.6H), 7.2 (d, 0.4H). |
| 54 | 1.7 (d, b, 3H), 2.3 (m, 2H), 2.7 (m, 2H), 3.7 (m, 1H), 3.8 (ds, 6H), 3.9 (s, 3H), 5.1 (m, 1H), 5.4 (m, 1H), 6.6 (d, 1H), 6.8 (d, 1H). |
| 55 | 1.5 (s, 3H), 2.2 (m, 2H), 2.6 (m, 1H), 3.2 (m, 1H), 3.9 (s, 6H), 4.0 (s, 3H), 4.2 (m, 1H), 5.8 (m, b, 2H), 6.6 (d, 1H), 7.1 (d, 1H). |
| 58 | 1.66–1.85 (m, 2H), 3.20–3.26 (m. 1H), 3.20–3.56 (m, 2H), 3.8 (s, 3H), 3.85 (s, 3H), 3.86 (s, 3H), 4.9 (t, 1H), 6.01–6.07 (dd, 1H), 6.58–6.64 (m, 1H), 6.62 (d, 1H), 6.87 (d, 1H) |
| 61 | 0.9 (d, 3H), 1.07 (d, 3H), 2.24–2.67 (m, 1H), 2.87–3.11 (m, 1H), 3.20–3.64 (m, 1H), 3.83 (s, 3H), 3.85 (s, 3H), 3.98 (s, 3H), 5.15–5.84 (m, 3H), 6.6 (d.1H), 6.70 (d, 1H) |
| 63 | 1.7–1.9 (m, 6H), 2.5 (m, 2H), 2.8 (m, 2H), 3.8 (s, 3H), 3.85 (s, 3H), 3.9 (s, 3H), 6.6 (d, 1H), 6.7 (d, 1H). |

The following preparative methods were used to synthesize the example compounds.

Method A: Preparation of Examples 1, 3, 5–17, 19–35, 46–51, 54–62 and 67.

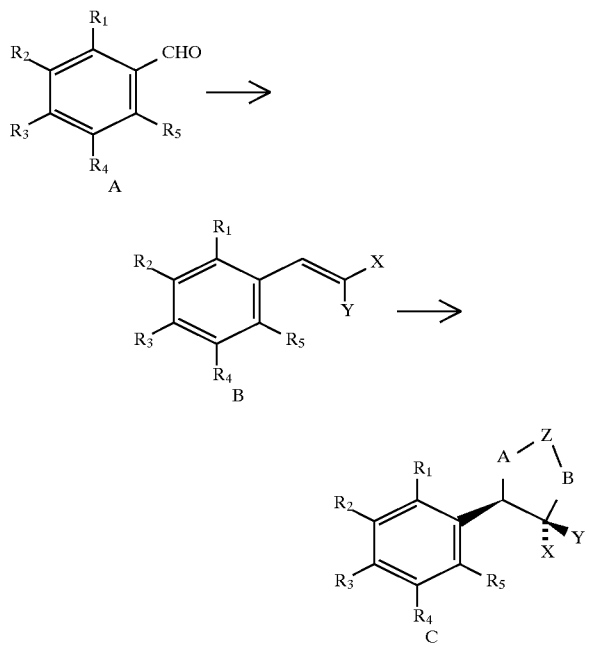

Example 1 is a known compound and can be made by Method A.
I. Formation of Aldehyde A Starting substituted benzaldehydes were available from commercial sources for Examples 1–23, 25–28, 30, 31, 35, 46, 52, 53, 54–62 and 67.

Aldehyde for example 50 was prepared via a method in The Dictionary of Organic Compounds V. 1965, p. 3111.

Aldehydes for examples 64–66 were prepared via a multistep procedure outlined in Comins, d. L.; Killpack, M. O. *J. Org. Chem.* 55, p 69–73 (1990).

Aldehydes for examples 68–76 were purchased from prof. Gronowitz of the University of Lund in Lund, Sweden a. Preparation of 3,4-Dimethoxy-2-nitrobenzaldehyde (aldehyde for Example 24)

Step 1—Formation of 4-Acetoxy-3-methoxybenzaldehyde

To 100 mL of water was added 50–60 mL of aqueous 50% sodium hydroxide followed by 50 g (0.33 mol) of vanillin. To this suspension was added at 0° C. 40–50 mL of acetic anhydride. After addition was complete the reaction was allowed to warm to room temperature and stirred for 6 hrs when the resultant white precipitate was collected by suction filtration. After drying 62.3 g (0.32 mol, 97%) of desired product was obtained as shown by $^1$H NMR.

Step 2—Formation of 4-Hydroxy-3-methoxy-2-nitrobenzaldehyde

To 300 mL of fuming nitric acid at −20° C. was added slowly 62.3 g (0.32 mol) of 4-acetoxy-3-methoxybenzaldehyde. The reaction was allowed to stir for one hour after which time the deep orange solution was poured carefully onto ice and the aqueous solution made basic (pH=10, 50% NaOH). This solution was filtered to remove suspended solids and the filtrate was acidified (pH= 2, conc. HCl). The resultant brown precipitate was collected by vacuum filtration and dried to give desired product as shown by $^1$H NMR.

Step 3—Formation of 3,4-Dimethoxy-2-nitrobenzaldehyde

To 7 g (35 mmol) of 4-hydroxy-3-methoxy-2-nitrobenzaldehyde in 200 mL of acetone was added 7.9 g (57 mmol) of potassium carbonate followed by 45 mL (0.72 mol) of iodomethane and the reaction was refluxed for 2.5 h. After cooling the reaction was filtered to remove solids and the filtrate evaporated to dryness in vacuo to give 7.0 g (33 mmol, 94%) of desired product as a semisolid.

b. Preparation of 2-Chloro-3,4-dimethoxybenzaldehyde (aldehyde for Example 29)

Step 1—Formation of 2-Chloro-3-hydroxy-4-methoxybenzaldehyde

Chlorine gas was bubbled through a solution of 50 g (0.33 mol) of isovanillin until a thick yellow precipitate formed. This precipitate was collected by vacuum filtration and the solids recrystallized from methanol to give 15.9 g (85 mmol, 26%) of a white solid shown to be desired product by $^1$H NMR.

Step 2—Formation of 2-Chloro-3,4-dimethoxybenzaldehyde

To 8.03 g (43 mmol) of 2-Chloro-3-hydroxy-4-methoxybenzaldehyde in 100 mL of acetonitrile was added 7.7 g (55 mmol) of powdered potassium carbonate followed by 8.3 mL (0.13 mol) of iodomethane. The reaction was slowly warmed to reflux where it was stirred for 24 h. After cooling to room temperature the suspension was filtered and the filtrate evaporated to dryness in vacuo to give 8.5 g (42 mmol, 98%) of a white solid shown to be desired product by $^1$H NMR.

c. Preparation of 2-Ethoxy-3,4-dimethoxybenzaldehyde (aldehyde for Example 32)

To 5.0 g (27 mmol) of 2-hydroxy-3,4-dimethoxybenzaldehyde in 100 mL of acetone was added 10 g (72 mmol) of potassium carbonate and 10–15 mL of iodoethane. The reaction was refluxed for 3 h before cooling to room temperature and gravity filtered. The filtrate was evaporated to dryness in vacuo to give 4.5 g (21 mmol) of an oil shown to be desired product by $^1$H NMR. Aldehydes for Examples 33, 34 and 47 were prepared in an analogous fashion using the appropriate amount of the necessary alkyl halide.

d. Preparation of 2,3,4-Trimethylbenzaldehyde (aldehyde for Example 48)

To a stirred solution of SnCl$_4$ (39 g, 0.15 mol) in 50 mL of dichloromethane was added dropwise at −5° C. a solution of 15 g (0.13 mol) of dichloromethylmethylether. This solution was stirred at −5° C. for one hour before adding dropwise over 10 min a solution of 12 g (0.1 mol) of 1,2,3-trimethylbenzene. The mixture was stirred at 0° C. for 15 min before warming to room temperature where it was stirred an additional 1.5 hrs. After quenching onto 100 g of ice the organic layer was separated, washed with water, saturated aqueous sodium bicarbonate and water before drying over Na$_2$SO$_4$, filtering and evaporating to dryness in vacuo. The product was purified by distillation in vacuo. B.p. 120°–122° C. (11 mm). Lit. b.p. 121.5 (11 mm) Yield: 9.2 g (70%).

e. Preparation of 2,4-Dimethoxy-3-ethylbenzaldehyde (aldehyde for Example 49)

To a mixture of 2-ethyl-1,3-dimethoxybenzene (16.5 g, 0.1 mol) and N-methylformanilide (14.2 g, 0.105 mol) was added dropwise keeping the temperature below 20° C. 16.9 g (0.11 mol) of POCl$_3$. The reaction was stirred at room temperature for one hour and then at 60° C. for 3 hrs. After cooling to room temperature the reaction was quenched with 50 g of ice, taken to pH=5–6 (5N NaOH) and extracted with diethyl ether. The organic phase was washed with 10% HCl and water before drying over Na$_2$SO$_4$, filtering and evaporating to dryness in vacuo. The product was recrystallized from 90% methanol to give 13.6 g (70%) mp=58°–59° C. 2-Ethyl-1,3-dimethoxybenzene was made from 2-ethyl-1,3-dihydroxybenzene using a procedure analogous to c. 2-Ethyl-1,3-dihydroxybenzene was prepared by a literature procedure in Organic Synthesis, Coll. Vol. 1 p. 211.

3,4-Dimethoxy-2-ethylbenzaldehyde (Example 51) was prepared in an analogous fashion from 2,3-dimethoxyethylbenzene which in turn was prepared by a literature method (Organic Reactions. 1, p.164.)

II. Ethylene Formation A to B

Ethylenes used as dienophiles in the Diels-Alder reaction outlined below were prepared in the following manner. For examples 1–9, 11, 12,14–35, 46, 47 50 and 54–62. the ethylenes were prepared in an analogous fashion to Worrall, David E. Organic Synthesis Coll. Vol 1. p. 413. For examples 10 and 13 the ethylenes were prepared using a method analogous to Bastus, J. B. Tetrahedron Letters 15, p.955 (1963). For examples 48, 49 and 51 the ethylenes were prepared in analogy to J. Org. Chem. 9, p.170 (1944).

For examples 64–67 the ethylenes were prepared in analogy to Bourguignon, J.; LeNard, G.; Queguiner, G. *Can. Journal of Chem.* 63, 2354 (1985).

For examples 68–76 the ethylenes were prepared in analogy to Williams, T. M.; Hudcoskey, R. J.; Hunt, C. A.; Shepard, K. L. *J. Heterocyclic Chem.* 28, 13 (1991).

III. Diels-Alder Reaction B to C

Examples 54–62, 64–76 were prepared in analogy to Dauben, W. G.; Kowalczyk, B. A.; Lichtenthaler, F. W. *J. Org. Chem.* 55, 2391 (1990) at pressures of from 12–16 kbar, tmperatures from 30°–80° C. in 24–72 hours.

To 10 mmol of dienophile in either dioxane or toluene was added 8–20 equivalents of diene (butadiene, substituted butadiene or butadiene sulfone) and a catalytic amount of radical initiator (either 3-t-butyl-4-hydroxy-5-methylphenyl sulfide or hydroquinone). This mixture was heated in a pressure vessel at 130° C. for 2–10 days. After cooling to room temperature and releasing the remaining pressure the residue was quenched with water and extracted with ethyl ether. The organic extracts were combined, dried, filtered and evaporated to dryness in vacuo and then chromatographed using an appropriate solvent system. Table III gives specific reaction conditions and yields for each example.

TABLE III

Reaction Conditions and Yields

| Ex. # | Solvent | Radical Initiator | Time | Diene | % Yield |
|---|---|---|---|---|---|
| 3 | toluene | A | 5 D | butadiene | 30% |
| 5 | toluene | A | 5 D | butadiene | 6% |
| 6 | toluene | A | 7 D | butadiene | 29% |
| 7 | toluene | A | 5 D | butadiene | 11% |
| 8 | toluene | A | 6 D | butadiene | 38% |
| 9 | toluene | A | 7 D | butadiene | not determined |
| 10 | dioxane | B | 9 D | butadiene sulfone | 15% |
| 11 | toluene | A | 10 D | 2,3-dimethylbutadiene | 81% |
| 12 | toluene | B | 7 D | butadiene sulfone | 35% |
| 13 | dioxane | B | 14 D | butadiene sulfone | 58% |
| 14 | toluene | B | 5 D | butadiene sulfone | 10% |
| 15 | toluene | B | 7 D | butadiene sulfone | 26% |
| 16 | toluene | B | 7 D | butadiene sulfone | 6% |
| 17 | dioxane | B | 2 D | butadiene sulfone | not determined |
| 19 | dioxane | B | 4 D | butadiene sulfone | 35% |
| 20 | dioxane | B | 3 D | butadiene sulfone | 31% |
| 21 | dioxane | B | 3 D | butadiene sulfone | 29% |
| 22 | dioxane | B | 6 D | butadiene sulfone | 13% |

TABLE III-continued

Reaction Conditions and Yields

| Ex. # | Solvent | Radical Initiator | Time | Diene | % Yield |
|---|---|---|---|---|---|
| 23 | dioxane | B | 4 D | butadiene sulfone | 13% |
| 24 | dioxane | B | 3 D | butadiene sulfone | 31% |
| 25 | dioxane | B | 3 D | butadiene sulfone | 5% |
| 26 | dioxane | B | 3 D | butadiene sulfone | 48% |
| 27 | dioxane | B | 2 D | butadiene sulfone | 21% |
| 28 | dioxane | B | 4 D | butadiene sulfone | 51% |
| 29 | dioxane | B | 4 D | butadiene sulfone | 36% |
| 30 | dioxane | B | 3 D | butadiene sulfone | not determined |
| 31 | dioxane | B | 5 D | butadiene sulfone | 6% |
| 32 | dioxane | B | 7 D | butadiene sulfone | 8% |
| 33 | dioxane | B | 8 D | butadiene sulfone | 10% |
| 34 | dioxane | B | 5 D | butadiene sulfone | 3% |
| 35 | dioxane | B | 3 D | 2-methylbutadiene | 14% |
| 46 | dioxane | B | 7 D | 2-methylbutadiene | 78% |
| 47 | dioxane | B | 7 D | butadiene sulfone | 43% |
| 48 | dioxane | B | 7 D | butadiene sulfone | 31% |
| 49 | dioxane | B | 7 D | butadiene sulfone | 36% |
| 50 | dioxane | B | 7 D | butadiene sulfone | 73% |
| 51 | dioxane | B | 7 D | butadiene sulfone | 55% |

A - 3-t-butyl-4-hydroxy-5-methylphenyl sulfide
B - Hydroquinone
D - Days

Method B: Preparation of Examples 36 and 37

Step 1—Preparation of 2-hydroxy-2-(2,3,4-trimethoxyphenyl)cyclohexanone

A stirred solution of 8.70 g (51.8 mmol) of 1,2,3-trimethoxybenzene and 8.25 mL (54.7 mmol) of tetramethylethylenediamine in 40 mL of THF was cooled in an ice bath and 24.0 mL of 2.5 molar n-BuLi in hexanes (60.0 mmol) was added dropwise over 20 min. The cooling bath was removed and the mixture was stirred at room temperature for 2 h. The mixture was cooled to −70° C. and a solution of 6.95 g (49.6 mmol) of 2-ethoxycyclohex-2-en-1-one in 30 mL of THF was added dropwise over 45 min. The cooling bath was removed and the mixture was stirred at room temperature for 2 days. The mixture was poured into 150 mL of 5% aqueous HCl and allowed to stand for 2 h. The mixture was extracted with two 80 mL portions of ether. The combined ether extracts were washed with 50 mL of saturated aqueous NaHCO$_3$, and dried over MgSO$_4$. Removal of the solvent left 13.56 g of an oil which was purified by flash chromatography on a column of 100 g of silica gel eluted successively with 250 mL portions of 0, 8, 16, 24, 40, 60, 80 and 100% ether in hexanes to furnish 7.08 g of 2-hydroxy-2-(2,3,4-trimethoxyphenyl)cyclohexanone as a solid, mp 88°–91° C. $^1$H-NMR (CDCl$_3$) d 1.5–1.8 (4H), 2.0 (m, 1H), 2.5 (m, 2H), 2.9 (m, 1H), 3.7 (s, 3H), 3.88 (s, 3H), 3.92 (s, 3H), 4.6 (s, 1H), 6.75 (d, 1H), 7.25 (d, 1H).

Step 2—Preparation of 2-(2,3,4-trimethoxyphenyl)-2-cyclohexen-1-one

A solution of 6.48 g (23.1 mmol) of 2-hydroxy-2-(2,3,4-trimethoxyphenyl)cyclohexanone in 100 mL of toluene was heated at reflux with a catalytic quantity of p-toluenesulfonic acid for 3 h. The mixture was cooled, diluted with 100 mL of ethyl acetate, washed with 50 mL of saturated aqueous NaHCO$_3$ and 50 mL of brine, and dried over MgSO$_4$. Removal of the solvent left 6.28 g of 2-(2,3,4-trimethoxyphenyl)-2-cyclohexen-1-one as a brown oil. $^1$H-NMR (CDCl$_3$) d 2.1 (m, 2H), 2.4–2.7 (4H), 3.8 (s, 3H), 3.9 (s, 6H), 6.65 (d, 1H), 6.8 (d, 1H), 6.9 (m, 1H).

Step 3—Preparation of 2-(2,3,4-trimethoxyphenyl)-cyclohexanone

To a solution of 6.20 g (23.5 mmol) of 2-(2,3,4-trimethoxyphenyl)cyclohex-2-en-1-one in 150 mL of ethanol was added a small quantity of 5% palladium on carbon and the mixture was shaken under 60–70 psi of hydrogen until hydrogen absorption ceased. The mixture was filtered through Celite® and the filtrate was concentrated on the rotovap to give 5.53 g of an oil. Flash chromatography on a column of 50 g of silica gel eluted successively with 200 mL portions of 0, 10, 20, 30, 40, 50 and 60% ether in hexanes furnished 4.00 g of 2-(2,3,4-trimethoxyphenyl)-cyclohexanone as a colorless oil. $^1$H-NMR (CDCl$_3$) d 1.7–2.3 (6H), 2.5 (m, 2H), 3.8 (s, 3H), 3.85 (s, 6H), 6.7 (d, 1H), 6.8 (d, 1H).

Step 4A—Preparation of 1-dimethylaminoimino-2-(2,3,4-trimethoxyphenyl)-cyclohexane (Example 36)

To a stirred solution of 0.81 g (3.07 mmol) of 2-(2,3,4-trimethoxyphenyl)-cyclohexanone and four drops of glacial acetic acid in 10 mL of ethanol was added 0.23 mL (3.03 mmol) of 1,1-dimethylhydrazine. The mixture was stirred for three days, diluted with 100 mL of water and extracted with two 100 mL portions of ether. The combined ether extracts were dried over MgSO$_4$ and evaporated in vacuo to leave 0.97 g of an oil. Flash chromatography on a column of 30 g of silica gel eluted successively with 100 mL portions of 25, 50, 75 and 100% ether in hexanes furnished 0.83 g of 1-dimethylaminoimino-2-(2,3,4-trimethoxyphenyl) cyclohexane (Example 36) as an oil.

Step 4B—Preparation of 1-methoxyimino-2-(2,3,4-trimethoxyphenyl)cyclohexane (Example 37)

To a stirred solution of 1.02 g (3.86 mmol) of 2-(2,3,4-trimethoxyphenyl)-cyclohexanone and 0.32 mL (4.0 mmol) of pyridine in 10 mL of ethanol was added 0.35 g (4.2 mmol) of methoxylamine hydrochloride. The mixture was stirred for 3 days at room temperature, diluted with 100 mL of water and extracted with two 100 mL portions of ether. The combined ether extracts were dried over MgSO$_4$. Removal of the solvent left 1.13 g of an oil. Flash chromatography on a column of 25 g of silica gel eluted successively with 100 mL portions of 20, 30, 40 and 50% ether in hexanes furnished 0.98 g of a mixture of E- and Z-1-methoxyimino-2-(2,3,4-trimethoxyphenyl)cyclohexane (Example 37) as an oil.

Method C: Preparation of 3-(2,3,4-trimethoxyphenyl)-2-methyl-4-nitroisoxazolidine (Example 38)

Step 1—Preparation of N-methyl-C-(2,3,4-trimethoxyphenyl)nitrone

To a stirred suspension of 9.97 g (50.9 mmol) of 2,3,4-trimethoxybenzaldehyde and 4.43 g (53.1 mmol) of N-methylhydroxylamine hydrochloride in 100 mL of ethanol was added a solution of 2.05 g (51.3 mmol) of sodium hydroxide in 15 mL of water. The mixture was stirred at room temperature for 22 h and evaporated in vacuo to remove the bulk of the solvent. The residual solid was taken up in 150 mL of dichloromethane, washed with 50 mL of water and dried over MgSO$_4$. Removal of the solvent afforded 11.31 g of N-methyl-C-(2,3,4-trimethoxyphenyl) nitrone as a white solid. $^1$H-NMR (CDCl$_3$) d 3.85–3.95 (9H), 6.75 (d, 1H), 7.65 (s, 1H), 9.1 (d, 1H).

Step 2—Preparation of 2-methyl-4-nitro-3-(2,3,4-trimethoxyphenyl)-isoxazolidine

A 5.88 g (26.1 mmol) portion of N-methyl-C-(2,3,4-trimethoxyphenyl)nitrone was added to 50 mL of 0.76 molar (38 mmol) nitroethylene in toluene. The mixture was heated at reflux for 2 h. The solvent was removed in vacuo to leave a brown tar which was purified by flash chromatography on a column of 50 g of silica gel eluted successively with 100 mL portions of 0, 10, 20, 30, 40 and 50% ether in hexanes to yield 4.53 g of an orange oil. This material was crystallized from 20 mL of ice-cold 1:1 ether:hexanes to give 3.16 g of 2-methyl-4-nitro-3-(2,3,4-trimethoxyphenyl)-isoxazolidine (Example 38) as a low melting solid.

Method D: Preparation of cis- and trans-4-nitro-3-(2,3,4-trimethoxyphenyl)-cyclohexene (Example 39) and 1-cyano-2-(2,3,4-trimethoxyphenyl)cyclohexane Example 42)

Step 1—Preparation of 4-hydroxy-4-(2,3,4-trimethoxyphenyl)butene

A stirred solution of 8.77 g (44.7 mmol) of 2,3,4-trimethoxybenzaldehyde in 100 mL of THF was cooled in an ice bath and 55 mL of 1.0 molar (55.0 mmol) allylmagnesium bromide in ether was added dropwise over 0.5 h. The cooling bath was allowed to warm up and the mixture was stirred overnight at room temperature. A 200 mL portion of 5% aqueous HCl was added and the mixture was extracted with two 200 mL portions of ether. The combined ether extracts were washed with 50 mL of saturated aqueous NaHCO$_3$, dried over MgSO$_4$ and the solvent removed in vacuo to leave 10.30 g of 4-hydroxy-4-(2,3,4-trimethoxyphenyl)butene as an oil. $^1$H NMR (CDCl$_3$) d 2.5 (m, 2H), 3.8 (s, 6H), 3.9 (s, 3H), 4.9 (t, 1H), 5.1 (m, 2H), 5.85 (m, 1H), 6.65 (d, 1H), 7.05 (d, 1H).

Step 2—Preparation of 1-(2,3,4-trimethoxyphenyl)-1,3-butadiene

A solution of 10.30 g (43.3 mmol) of 4-hydroxy-4-(2,3,4-trimethoxyphenyl)-butene and 15 mL (107 mmol) of triethylamine in 100 mL of dichloromethane was cooled in an ice bath and 3.7 mL (47.6 mmol) of methanesulfonyl chloride was added dropwise over 5 min. The ice bath was allowed to expire and the mixture was stirred overnight. The mixture was diluted with 300 mL of ether, washed with two 100 mL portions of 5% aqueous HCl and 100 mL of saturated aqueous NaHCO$_3$, dried over MgSO$_4$ and the solvent removed in vacuo to leave 8.14 g of crude 1-(2,3,4-trimethoxyphenyl)-1,3-butadiene as an orange oil.

Step 3A—Preparation of cis- and trans-ethyl 2-(2,3,4-trimethoxyphenyl)cyclohex-3-ene-1-carboxylate A solution of 4.10 g (18.6 mmol) of crude 1-(2,3,4-trimethoxyphenyl)-1,3-butadiene and 2.0 mL (18.5 mmol) of ethyl acrylate in 50 mL of toluene was heated at reflux for 3 days. The mixture was evaporated in vacuo and the residue was purified by flash chromatography on a column of 100 g of silica gel eluted successively with 250 mL portions of 10, 20, 30, 40, 50, 60, and 80% ether in hexanes and 75 mL fractions were collected. Fractions 10–13 were combined and concentrated to furnish 2.77 g of cis- and trans-ethyl 2-(2,3,4-trimethoxyphenyl)cyclohex-3-ene-1-carboxylate. $^1$H NMR (CDCl$_3$) d 1.1 (s, 3H), 1.8–3.1 (m, 1H), 3.8 (s, 6H), 3.85 (s, 3H), 3.9 (q, 2H), 3.95–4.2 (m, 2H), 6.7 (m, 1H), 6.9 (m, 1H), 6.6 (d, 1H), 6.9 (d, 1H).

Step 3B—Preparation of trans-4-nitro-3-(2,3,4-trimethoxyphenyl)cyclohexene (Example 39)

To a stirred solution of 6.33 g (28.8 mmol) of crude 1-(2,3,4-trimethoxyphenyl)-1,3-butadiene in 30 mL of toluene was added 25 mL of 1.5M (37.5 mmol) nitroethylene in toluene. The mixture was heated at reflux for 1 h, cooled to room temperature and diluted with 100 mL of ether. The mixture was washed with 50 mL of 5% aqueous HCl and 50 mL of saturated aqueous NaHCO$_3$, and dried over MgSO$_4$. Removal of the solvent left 6.51 g of a dark brown oil which was purified by flash chromatography on silica gel, eluting with an ether hexane gradient to afford 0.74 g of cis- and trans-4-nitro-3-(2,3,4-trimethoxyphenyl)cyclohexene as an oil. This material was dissolved in 25 mL of methanol and 10 drops of 25% sodium methoxide in methanol were added. The mixture was heated at reflux for 18 h, cooled, diluted with 150 mL of water and extracted with two 200 mL portions of ether. The combined ether extracts were washed with 50 mL of brine and dried over $MgSO_4$. Removal of the solvent gave 0.65 g of a brown oil which was purified by flash chromatography on a column of 10 g of silica gel eluted successively with 100 mL portions of 10, 20 and 30% ether in hexanes to afford 0.34 g of trans-4-nitro-3-(2,3,4-trimethoxyphenyl)cyclohexene (Example 39) as an oil.

Step 4—Preparation of cis- and trans-ethyl 2-(2,3,4-trimethoxyphenyl)cyclohexane-1-carboxylate A solution of 2.77 g (8.99 mmol) of ethyl 2-(2,3,4-trimethoxyphenyl)cyclohex-3-ene-1-carboxylate in 50 mL of ethyl acetate was sparged with nitrogen and a small amount of 10% palladium on carbon was added. The mixture was shaken under 50 psi of hydrogen for 2 h and filtered through Celite® diatomaceous earth. The filtrate was concentrated to leave 2.64 g of cis- and trans-ethyl 2-(2,3,4-trimethoxyphenyl)cyclohexane-1-carboxylate as a yellowish oil. $^1$H NMR ($CDCl_3$) _1.0 (t, 3H), 1.3–3.3 (m, 10H), 3.8 (s, 3H), 3.85 (s, 3H), 3.9 (q, 2H) 3.95 (s, 3H), 6.6 (d, 1H), 6.9 (d, 1H)

Step 5—Preparation of trans-ethyl 2-(2,3,4-trimethoxyphenyl)cyclohexane-1-carboxylate To a solution of 2.64 g of cis- and trans-ethyl 2-(2,3,4-trimethoxyphenyl)cyclohexane-1-carboxylate in 20 mL of dry THF were added 1.08 g (9.6 mmol) of potassium t-butoxide and 0.5 mL of t-butanol. The mixture was heated at reflux for 1 h, cooled, diluted with 100 mL of 5% aqueous NaOH and extracted with two 100 mL portions of ether. The combined ether extracts were dried over $MgSO_4$ and the solvent removed in vacuo to leave 1.78 g of trans-ethyl 2-(2,3,4-trimethoxyphenyl)cyclohexane-1-carboxylate as an oil. $^1$H NMR ($CDCl_3$) _1.0 (t, 3H), 1.3–2.1 (m, 8H), 2.7 (m, 1H), 3.1 (m, 1H), 3.8 (s, 3H), 3.85 (s, 3H), 3.9 (q, 2H), 3.95 (s, 3H), 6.6 (d 1H), 6.9 (d, 1H).

Step 6—Preparation of trans-2-(2,3,4-trimethoxyphenyl)cyclohexane-1-carboxylic acid To a stirred solution of 1.22 g (3.8 mmol) of trans-ethyl 2-(2,3,4-trimethoxyphenyl)cyclohexane-1-carboxylate in 20 mL of THF and 10 mL of methanol was added 10 mL of 10% aqueous NaOH. The mixture was stirred at room temperature for 18 h and heated at reflux for 18 h. After cooling, the bulk of the organic solvents was removed in vacuo and the residue was diluted with 100 mL of 5% aqueous NaOH and washed with 100 mL of ether. The aqueous layer was acidified to pH 1 with concentrated HCl and extracted with two 100 mL portions of ether. These ether extracts were combined, dried over $MgSO_4$ and the solvent removed in vacuo to leave 0.88 g of trans-2-(2,3,4-trimethoxyphenyl) cyclohexane-1-carboxylic acid as an oil. $^1$H NMR ($CDCl_3$) _ 1.3–2.2 (m, 8H), 2.65 (m, 1H), 3.1 (m, 1H), 3.8 (s, 9H), 6.6 (d, 1H), 6.8 (d, 1H).

Step 7—Preparation of trans-2-(2,3,4-trimethoxyphenyl) cyclohexane-1-carboxamide (Example 41)

A stirred solution of 1.98 g (6.7 mmol) of trans-2-(2,3,4-trimethoxyphenyl)cyclohexane-1-carboxylic acid in 30 mL of dichloromethane was cooled in an ice bath and five drops of DMF were added, followed by 0.62 mL (7.1 mmol) of oxalyl chloride. The mixture was stirred in the ice bath for 1.5 h and poured into 50 mL of concentrated aqueous ammonium hydroxide. The mixture was stirred overnight, diluted with 100 mL of 5% aqueous NaOH and extracted with three 70 mL portions of ethyl acetate. The combined ethyl acetate extracts were washed with 25 mL of brine, dried and evaporated in vacuo to leave 1.91 g of a brown tarry material. This material was purified by flash chromatography on a column of 25 g of silica gel eluted successively with 100 mL portions of 0, 20, 40, 60, 80 and 100% ethyl acetate in hexanes to afford 1.49 g of trans-2-(2,3,4-trimethoxyphenyl)cyclohexane-1-carboxamide (Example 41) as a tan solid, mp 45°–48° C.

Step 8—Preparation of trans-1-cyano-2-(2,3,4-trimethoxyphenyl)cyclohexane

To a stirred solution of 1.05 g (3.58 mmol) of trans-2-(2, 3,4-trimethoxyphenyl)-cyclohexane-1-carboxamide in 5 mL of THF and 5 mL of $CCl_4$ was added 1.88 g (7.17 mmol) of triphenylphosphine. The mixture was stirred at 50° C. for 2 h. The mixture was diluted with 70 mL of ethyl acetate, washed with 50 mL of 5% aqueous HCl and 50 mL of saturated aqueous $NaHCO_3$, and dried over $MgSO_4$. Removal of the solvent left 2.38 g of a tan solid which was purified by flash chromatography on a column of 30 g of silica gel eluted successively with 100 mL portions of 0, 10, 20, 30, 40, 50 and 60% ether in hexanes to afford 0.77 g of trans-1-cyano-2-(2,3,4-trimethoxyphenyl)cyclohexane (Example 42) as a white solid, mp 69°–72° C.

Method E: Preparation of 4-nitro-5-(5-bromo-2,3,4-trimethoxyphenyl)cyclohexene (Example 43)

To a stirred solution of 0.77 g (2.63 mmol) of Compound 12 in 15 mL of dichloromethane was added 2.75 mL of 1.0 molar (2.75 mmol) bromine in $CCl_4$. The mixture was stirred at room temperature for 3 h, diluted with 70 mL of ether, washed with 25 mL of saturated aqueous NaHSO3 and 25 mL of saturated aqueous $NaHCO_3$, and dried over $MgSO_4$. Removal of the sovent afforded 1.01 g of a white solid which was combined with 0.38 g of product from another run and purified by flash chromatography on a column of 25 g of silica gel eluted successively with 100 mL portions of 0, 10, 20 and 30% ether in hexanes to afford 0.97 g of 4-nitro-5-(5-bromo-2,3,4-trimethoxyphenyl)cyclohexene (Example 43) as a white solid, mp 134°–136° C.

Method F: Preparation of 4-bromo-4-nitro-5-(2,3,4-trimethoxyphenyl)cyclohexene (Example 44)

To a stirred solution of 0.74 g (2.53 mmol) of Example 12 in 15 mL of dichloromethane was added 0.64 g (2.96 mmol) of 25% sodium methoxide in methanol. The mixture was stirred for 10 min and 2.65 mL of 1.0M bromine in CCl4 was added dropwise over 2 min. The mixture was stirred at room temperature for 3 h, diluted with 75 mL of ether, washed with 25 mL of water and 25 mL of brine and dried over $MgSO_4$. Removal of the solvent in vacuo left 1.00 g of a brown oil. This was combined with 0.38 g of crude product from another run and purified by flash chromatography on a column of 30 g of silica gel eluted successively with 100 mL portions of 0, 10, 20, 30 and 40% ether in hexanes to furnish 0.56 g of 4-bromo-4-nitro-5-(2,3,4-trimethoxyphenyl) cyclohexene Example 44) as a colorless oil.

Method G: Preparation of 1-nitro-2-(2,3,4-trimethoxyphenyl)cyclopentane (Example 45)

Step 1—Preparation of 1, 1-ethylenedioxy-5-nitro-4-(2,3, 4-trimethoxyphenyl)-pentane A 2.16 g (90 mmol) portion of magnesium turnings was stirred vigorously under nitrogen with a Teflon coated magnetic stir bar for 16 h. A crystal of iodine and 10 mL of dry THF were added. About 10% of 10 mL of 2-(2-bromoethyl)-1,3-dioxolane was added. An exothermic reaction occurred. The mixture was diluted with an additional 90 mL of THF and the remaining 90% of the bromide was added dropwise over 45 min, The mixture was stirred for a further 3 h at room temperature and added dropwise over 20 min to an ice-cold solution of 18.48 g (77.3 mmol) of 1-nitro-2-(2,3,4-trimethoxyphenyl)ethene in 100 mL of THF. The cooling bath was removed, the mixture was stirred at room temperature for 20 h, poured into 500 mL of ice cold 3% aqueous HCl and extracted with three 200 mL portions of ether. The combined ether extracts were washed with 200 mL of saturated aqueous $NaHCO_3$ and 200 mL of brine and dried over $MgSO_4$. Removal of the solvent in vacuo left 17.14 g of an orange oil. This material was purified by flash chromatography on a column of 100 g of silica gel eluted successively with 250 mL portions of 0, 10, 20, 30, 40, 50, 60, 70, 80 and 100% ether in hexanes and 75 mL fractions were collected. Fractions 23–27 were combined and evaporated in vacuo to afford 5.53 g of 1,1-ethylenedioxy-5-nitro-4-(2,3,4-trimethoxyphenyl)pentane as an oil. $^1H$ NMR $(CDCl_3)$ _1.5–1.9 (m, 4H), 3.7–4.0 (1 m, 14H), 4.6 (m, 2H), 4.85 (m, 1H), 6.6 (d, 1H), 6.8 (d, 1H).

Step 2—Preparation of 5-nitro-4-(2,3,4-trimethoxyphenyl)pentanal

To a stirred solution of 7.03 g (21.5 mmol) of 1,1-ethylenedioxy-5-nitro-4-(2,3,4-trimethoxyphenyl)pentane in 150 mL of THF was added 50 mL of 5% aqueous HCl. The mixture was stirred for 3 days. An additional 50 mL of 5% aqueous HCl was added and stirring was continued for 1 day. The bulk of the THF was removed in vacuo and the residue was extracted with 150 mL of ether. The ether solution was washed with two 50 mL portions of saturated aqueous $NaHCO_3$ and dried over $MgSO_4$. Removal of the solvent left 6.55 g of crude 5-nitro-4-(2,3,4-trimethoxyphenyl)pentanal as a yellow oil. $^1H$ NMR $(CDCl_3)$ _1.9–2.5 (m, 4H), 3.7–4.1 (m, 9H), 4.7 (m, 2H), 6.65 (d, 1H), 6.8 (d, 1H), 9.7 (s, 1H).

Step 3—Preparation of 1-nitro-5-(2,3,4-trimethoxyphenyl)cyclopentene (Example 40)

To a stirred solution of 6.55 g (22.1 mmol) of crude 5-nitro-4-(2,3,4-trimethoxyphenyl)pentanal in 50 mL of methanol was added 5.35 g of 25% sodium methoxide in methanol. The mixture was stirred at room temperature for 2 days. About half of the methanol was removed on the rotovap and 100 mL of 5% aqueous HCl was added to the residue. The mixture was extracted with two 100 mL portions of ether. The combined ether extracts were washed with 50 mL of brine, dried over $MgSO_4$ and the solvent removed in vacuo to afford 5.18 g of a brown oil. This material was purified by flash chromatography on a column of 80 g of silica gel eluted successively with 200 mL portions of 0, 10, 20, 30, 40 and 50% ether in hexanes to furnish 1.78 g of 1-nitro-5-(2,3,4-trimethoxyphenyl)cyclopentene (Example 40) as a yellow solid.

Step 4—Preparation of 1-nitro-2-(2,3,4-trimethoxyphenyl)cyclopentane (Example 45)

A stirred solution of 1.78 g (6.4 mmol) of 1-nitro-5-(2,3,4-trimethoxyphenyl)-cyclopentene in 40 mL of THF and 40 mL of methanol was cooled in an ice bath and a 0.35 g (9.2 mmol) portion of solid $NaBH_4$ was added. The mixture was stirred for 1 h and 0.38 g (10.0 mmol) of solid $NaBH_4$ was added. The mixture was stirred for 1 h and 0.37 g (9.8 mmol) of solid $NaBH_4$ was added. After stirring for 1 h, 100 mL of 5% aqueous HCl was added and the bulk of the THF and methanol were removed in vacuo. The residue was extracted with two 100 mL portions of ether. The combined ether extracts were washed with 30 mL of brine, dried over $MgSO_4$ and the solvent removed in vacuo to leave 1.37 g of an oil. The crude product was purified by flash chromatography on a column of 30 g of silica gel eluted successively with 100 mL portions of 0, 10, 20, 30, 40, 50 and 60% ether in hexanes to afford 0.68 g of a 1:1 mixture of cis- and trans-1-nitro-2-(2,3,4-trimethoxyphenyl)cyclopentane (Example 45).

Method H—Preparation of 4-Cyano-5-(2,3,4-trimethoxyphenyl)cyclohexene (Example 53)

Step 1—Preparation of 4-carboxy-4-cyano-5-(2,3,4-trimethoxyphenyl)cyclohexene (Example 52)

To 1.5 g (4.34 mmol) of 4-cyano-4-ethoxycarbonyl-5-(2,3,4-trimethoxyphenyl)-cyclohexene in 25 mL of tetrahydrofuran was added 12.5 mL of methanol and 5 mL of 50% sodium hydroxide before stirring at room temperature overnight. The reaction was quenched onto 50 mL of 10% aq. HCl and extracted with ethyl acetate (2×50 mL). The organics were combined, dried over $MgSO_4$, filtered and evaporated to dryness in vacuo to give 1.1 g (3.46 mmol, 80%) of white solid shown to be desired product by $^1H$ NMR.

Step 2—Preparation of 4-Cyano-5-(2,3,4-trimethoxyphenyl)cyclohexene (Example 53)

To 1.1 g (3.47 mmol) of 4-carboxy-4-cyano-5-(2,3,4-trimethoxyphenyl)cyclohexene was added 15 mL of methyl sulfoxide and heated at 160° C. for 18 h After cooling to room temperature the reaction was quenched onto 50 mL of water and extracted with ethyl ether (2×35 mL). The organics were combined, washed with water (2×50 mL), dried over $MgSO_4$, filtered and evaporated to dryness in vacuo. The residue was chromatographed (preparative thin layer, 1:1 hexanes/ethyl acetate) to give a yellow oil (250 mg, 0.91 mmol, 25%) of a 5:4 mixture of diastereomers of desired product as shown by $^1H$ NMR.

Method I—Preparation of 1-Nitro-2-(3,4-dimethoxyphenyl)cyclohexane (Example 2)

To 10 mmol of 4-nitro-5-(3,4-dimethoxyphenyl) cyclohexene in 100 mL of ethyl acetate was added 200 mg of 10% palladium on carbon. The resulting suspension was shaken at 50 psi of hydrogen on a Parr Apparatus for one hour. The catalyst was removed by filtration through Celite® diatomaceous earth and the filtrate evaporated to dryness in vacuo to give a 91% yield of the desired product based on $^1H$ NMR.

Method J—Preparation of Example 63

Step 1—Preparation of 1-(2,3,4-trimethoxyphenyl) cyclohexanol

To 8.7 g (51.8 mmol) of 1,2,3-trimethoxybenzene and 8.25 mL (54.7 mmol) of tetramethylethylenediamine in 40 mL of tetrahydrofuran (THF) at 0° C. was added dropwise over 15 min 37.5 mL (60 mmol) of 1.6M n-butyllithium in hexanes. Once addition was complete the ice bath was removed and the reaction stirred for two hours. It was then cooled to −78° C. where a solution of 5.9 mL (50 mmol) of cycloheptanone in 30 mL of THF was added over 30 min. The cooling bath was removed and the reaction stirred at room temperature overnight. Quenched onto 200 mL of 1M HCl, extracted with ethyl acetate (2×200 mL), organics were combined, washed with saturated NaCl (1×200 mL), dried over sodium sulfate, filtered and evaporated to dryness in vacuo. The crude product was chromatographed (flash, 5:1 hexanes/ethyl acetate) to give 11 g (38.5 mmol, 77%) of desired product as shown by $^1$H NMR (CDCl$_3$, 200 MHz) d 1.5–1.9 (m, 8H), 2.1 (m, 4H), 3.8 (ds, 6H), 4.0 (s, 3H), 4.1 (s, 1H), 6.6 (d, 1H), 7.0 (d, 1H).

Step 2—Preparation of 1-(2,3,4-trimethoxyphenyl) cycloheptene

To 9.0 g (32 mmol) of 1-(2,3,4-trimethoxyphenyl) cycloheptanol in 100 mL of toluene was added a catalytic amount of toluensulfonic acid monohydrate and refluxed for two hours. The reaction was cooled to room temperature where the solvent was removed in vacuo. The residue was partitioned between saturated sodium bicarbonate and ethyl acetate, the layers were separated and the organic dried over sodium sulfate before filtering and evporating to dryness in vacuo. The crude product was purifed by flash chromatography (5% ethyl acetate/hexanes) to give a clear oil 3.5 g (13.3 mmol, 39%) shown by $^1$H NMR to be desired product. $^1$H NMR (CDCl$_3$, 200 MHz) d 1.5–1.7 (m, b, 4H), 1.85 (m, b, 2H), 2.25 (m, 2H), 2.5 (m, 2H), 3.9 (s, 9H), 5.8 (t, 1H), 6.6 (d, 1H), 6.8 (d, 1H).

Step 3—Preparation of 1-nitro-2-(2,3,4-trimethoxyphenyl)cycloheptane (Example 63)

To 1.16 g (7.6 mmol) of silver nitrate in 40 mL of diethylether was added 1.93 g (7.6 mmol) of iodine and stirred at room temperature for one hour. To this mixture was added a solution of 1.0 g (3.8 mmol) of 1-(2,3,4-trimethoxyphenyl)cycloheptene and 1.3 mL (15.2 mmol) of pyridine in 10 mL of diethylether. the reaction was stirred at room temperature for 18 hours. The solids were removed by filtration and washed with diethyl ether. The filtrate was treated with 1 mL of triethylamine and evaporated to dryness in vacuo. The residue was dissolved in 3 mL of dichloromethane, treated with 2 mL of triethylamine and stirred at room temperature for one hour. The solvent was removed in vacuo. The residue was dissolved in dichloromethane (50 mL), washed with 5% sodium hydrogen sulfite (1×50 mL), 1N HCl (1×50 mL), saturated sdoium bicarbonate (1×50 mL) and warer (1×50 mL) before drying over sodium sulfate, filtering and evaporating to dryness in vacuo. Residue flash chromatographed in 5% ethyl acetate/hexanes to give 640 mg (2.08 mmol, 58%) of a yellow oil shown to be desired product by $^1$H NMR (CDCl$_3$, 200 MHz) d 1.7–1.9 (m, 6H), 2.5 (m, 2H), 2.8 (m, 2H), 3.8 (s, 3H), 3.85 (s, 3H), 3.9 (s, 3H), 6.6 (d, 1H0, 6.7 (d, 1H).

Examples 4 and 18 were prepared in an analogous fashion in 70% and 36% yield respectively.

The method, compounds, and compositions of this invention are useful as both preemergence and postemergence herbicides on both monocot and dicot weeds. In general, they require lower doses to control weeds preemergence. Preemergence herbicides are usually applied to the soil either before, during or after seeding, but before the crop emerges. Postemergence herbicides are applied after the plants have emerged and during their growth period. The compounds and compositions generally show selectivity to several agronomically important crops such as corn and rice.

Under some conditions the compounds of the invention may be incorporated into the soil or other growth medium prior to planting a crop. This incorporation may be by any convenient means, including mixing with the soil, applying the compound to the surface of the soil and then discing or dragging into the soil to the desired depth, or by employing a liquid carrier.

The compounds of the present invention can be applied to various loci such as the soil or foliage. For such purposes these compounds can be used in the technical or pure form as prepared, as solutions, or as formulations. Solutions and formulations of the compounds may contain from 0.01 to 99.9 percent by weight of the compound. More typically the solutions and formulations will contain from 1.0 to 85 percent by weight of the compound. The compounds are usually taken up in a carrier or are formulated so as to render them suitable for subsequent dissemination as herbicides. For example, these chemical agents can be formulated as solutions, wettable powders, emulsifiable concentrates, dusts, granular formulations, pellets, aerosols, or flowable emulsion concentrates. In such formulations, the compounds are extended with liquid or solid carriers and, when desired, suitable surfactants are incorporated.

It is usually desirable, particularly in the case of foliar spray formulations; to include one or more adjuvants, such as wetting agents, spreading agents, dispersing agents, stickers, adhesives, emulsifying agents and the like in accordance with agricultural practices. Such adjuvants commonly used in the art can be found in the John W. McCutcheon, Inc. publication "Detergents and Emulsifiers, Annual." Allured Publishing Company, Ridgewood, N.J., U.S.A.

The compounds can be applied as herbicidal sprays by methods commonly employed, such as conventional high-liter hydraulic sprays, low-liter sprays, air-blast spray, aerial sprays, and dusts. The dilution and rate of application will depend upon the type of equipment employed, the method of application, crop treated, and weeds to be controlled, but the effective amount is usually from 0.01 Kg. to 10 Kg. of the compound per hectare. Preferred amounts are from 0.1 Kg to 4 Kg of the compound per hectare.

As a soil treatment the compound can be incorporated in the soil or applied to the surface of the soil, usually at a rate of from 0.01 Kg. to 10 Kg. of the active ingredient per hectare. Again, preferred amounts are from 0.1 Kg to 4 Kg of the compound per hectare. As a foliar spray, the compound is usually applied to growing plants at similar rates.

The compounds of the invention can also be mixed with fertilizers or fertilizing materials before their application. In one type of solid fertilizing composition, particles of a fertilizer or fertilizing ingredients, such as ammonium sulfate, ammonium nitrate, or ammonium phosphate, can be coated with one or more of the compounds. The solid compounds and solid fertilizing material can also be admixed in mixing or blending equipment, or they can be incorporated with fertilizers in granular formulations. Any relative proportion of fertilizer can be used which is suitable for the crops and weeds to be treated. The compounds of the invention will commonly comprise from 5% to 25% of the fertilizing composition. These compositions provide fertilizing materials which promote the rapid growth of desired plants, and at the same time control the growth of undesired plants.

For some applications, one or more other herbicides may be added to the herbicides of the present invention, thereby providing additional advantages and effectiveness. When mixtures of herbicides are employed, the relative proportions which are used will depend upon the relative efficacy of compounds in the mixture with respect to the crops and weeds to be treated. Examples of other herbicides which can be combined with those of the present invention include:

CARBOXYLIC ACIDS AND DERIVATIVES 2,3,6-trichlorobenzoic acid and its salts;
2,3,5,6-tetrachlorobenzoic acid and its salts;
2-methoxy-3,5,6-trichlorobenzoic acid and its salts;

2-methoxy-3,6-dichlorobenzoic acid and its salts;
2-methyl-3,6-dichlorobenzoic acid and its salts;
2,3-dichloro-6-methylbenzoic acid and its salts;
2,4-dichlorophenoxyacetic acid and its salts and esters;
2,4,5-trichlorophenoxyacetic acid and its salts and esters;
2-methyl-4-chlorophenoxyacetic acid and its salts and esters;
2-(2,4,5-trichlorophenoxy)propionic acid and its salts and esters;
4-(2,4-dichlorophenoxy)butyric acid and its salts and esters;
4-(2-methyl-4-chlorophenoxy)butyric acid and its salts and esters;
2,3,6-trichlorophenylacetic acid and its salts;
3,6-endoxohexahydrophthahic acid and its salts;
dimethyl 2,3,5,6-tetrachloroterephthalate; trichloroacetic acid and its salts;
2,2-dichloropropionic acid and its salts;
2,3-dichloroisobutyric acid and its salts;
isopropylammonium 2-(4-isopropyl-4-methyl-5-oxo-2-imidazolin-2-yl)nicotinate;
2-[4,5-dihydro-4-methyl-4-(1-methylethyl)-5-oxo-1H-imidazol-2-yl]-3-quinolinecarboxylic acid;
6-(4-isopropyl-4-methyl-5-oxo-2-imidazolin-2-yl)-m-toluic acid, methyl ester and
6-(4-isopropyl-4-methyl-5-oxo-2-imidazolin-2-yl)-p-toluic acid, methyl ester;
N-(phosphomethyl)glycine isopropylammonium salt;
[3,5,6-trichloro-(2-pyridinyl)oxy]acetic acid;
3,7-dichloro-8-quinolinecarboxylic acid;
ammonium DL-homoalanin-4-yl(methyl)phosphinate;

CARBAMIC ACID DERIVATIVES ethyl N,N-di(n-propyl)thiolcarbamate;
n-propyl N,N-di(n-propyl)thiolcarbamate;
ethyl N-ethyl-N-(n-butyl)thiolcarbamate;
n-propyl N-ethyl-N-(n-butyl)thiolcarbamate;
2-chloroallyl N,N-diethyldithiocarbamate;
isopropyl N-phenylcarbamate;
isopropyl N-(m-chlorophenyl)carbamate;
4-chloro-2-butynyl-N-(m-chlorophenyl)carbamate;
methyl N-(3,4-dichlorophenyl)carbamate;
dinitro-o-(sec-butyl)phenol and its salts;
pentachlorophenol and its salts
S-(4-chlorobenzyl)-N,N-diethylthiolcarbamate;

SUBSTITUTED UREAS 2-chloro-N-[(4-methoxy-6-methyl-1,3,5-triazin-2-yl)aminocarbonyl]-benzenesulfon-amide;
3-(3,4-dichlorophenyl)-1,1-dimethylurea;
3-phenyl-1,1-dimethylurea;
3-(3,4-dichlorophenyl)-3-methoxy-1,1-dimethylurea;
3-(4-chlorophenyl)-3-methoxy-1,1-dimethylurea;
3-(3,4-dichlorophenyl)-1-n-butyl-1-methylurea;
3-(3,4-dichlorophenyl)-1-methoxy-1-methylurea;
3-(4-chlorophenyl)-1-methoxy-1-methylurea;
3-(3,4-dichlorophenyl)-1,1,3-trimethylurea;
3-(3,4-dichlorophenyl)diethylurea;
N-(4-isopropylphenyl)-N,N'-dimethylurea;
dichloral urea;
methyl 2-[[[[(4,6-dimethyl-2-pyrimidinyl)amino]-carbonyl]amino]sulfonyl]benzoate;
N-((6-methoxy-4-methyl-1,3,5-triazin-2-yl)aminocarbonyl)-2-(2-chloroethoxy)benzenesulfonamide;
2-[[[(4-chloro-6-methoxypyrimidine-2-yl)aminocarbonyl]amino]-sulfonyl]benzoic acid, ethyl ester;
methyl 2-[[[[(4-methoxy-6-methyl-1,3,5-triazin-2-yl)amino]-carbonyl]amino]-sulfonyl]benzoate;
methyl 3-[[(4-methoxy-6-methyl-1,3,5-triazin-2-yl)aminocarbonyl]aminosulfonyl]-2-thio-phenecarboxylate;
methyl 2-[[[[[(4,6-dimethoxypyrimidin-2-yl)amino]carbonyl]amino]sulfonyl]methyl]benzoate;
methyl 2-[[[[(4-methoxy-6-methyl-1,3,5-triazin-2-yl)methylamino]carbonyl]amino]-sulfonyl]benzoate;

SUBSTITUTED TRIAZINES 2-chloro-4,6-bis(ethylamino)-s-triazine;
2-chloro-4-ethylamino-6-isopropylamino-s-triazine;
2-chloro-4,6-bis(3-methoxy-n-propylamino)-s-triazine;
2-methoxy-4,6-bis(isopropylamino)-s-triazine;
2-chloro-4-ethylamino-6-(3-methoxy-n-propylamino)-s-triazine;
2-methylmercapto-4,6-bis(isopropylamino)-s-triazine;
2-methylmercapto-4,6-bis(ethylamino)-2-triazine;
2-methylmercapto-4-ethylamino-6-isopropylamino-s-triazine;
2-chloro-4,6-bis(isopropylamino)-s-triazine;
2-methoxy-4-ethylamino-6-isopropylamino-s-triazine;
2-methylmercapto-4-(2-methoxyethylamino)-6-isopropylamino-s-triazine;
4-amino-6-(t-butyl)-3-(methylthio)-1,2,4-triazine-5(4H)-one;

DIPHENYL ETHER DERIVATIVES 2,4-dichloro-4'-nitrodiphenyl ether;
2,4,6-trichloro-4'-nitrodiphenyl ether;
2,4-dichloro-6-fluoro-4'-nitrodiphenyl ether;
3-methyl-4'-nitrodiphenyl ether;
3,5-dimethyl-5'-nitrodiphenyl ether;
2,4'-dinitro-4-(trifluoromethyl)diphenyl ether;
2,4-dichloro-3'-methoxy-4'-nitrodiphenyl ether;
sodium 5-(2-chloro-4-(trifluoromethyl)phenoxy)-2-nitrobenzoate;
2-chloro-1-(3-ethoxy-4-nitrophenoxy)-4-(trifluoromethyl)benzene;
1-(carboethoxy)ethyl 5-[2-chloro-4-(trifluoromethyl)-phenoxy]-2-nitrobenzoate;
5-[2-chloro-4-(trifluoromethyl)phenoxyl]-N-(methylsulphony)-2-nitrobenzamide;

ANILIDES 2-chloro-N-(2-ethyl-6-methylphenyl)-N-(2-methoxy-1-methylethyl)acetamide;
2-chloro-2',6'-diethyl-N-(2-propyloxyethyl)acetanilide;
N-(3,4-dichlorophenyl)propionamide;
N-(3,4-dichlorophenyl)methacrylamide;
N-(3-chloro-4-methylphenyl)-2-methylpentanamide;
N-(3,4-dichlorophenyl)trimethylacetamide;
N-(3,4-dichlorophenyl)-alpha,alpha-dimethylvaleramide;
N-isopropyl-N-phenylchloroacetamide;
N-n-butoxymethyl-N-(2,6-diethylphenyl)chloroacetamide;
N-methoxymethyl-N-(2,6-diethylphenyl)chloroacetamide;

OXYPHENOXY HERBICIDES 2-(4-(2,4-dichlorophenoxy)phenoxy)methyl propionate;
methyl 2-(4-(3-chloro-5-(trifluoromethyl)-2-pyridinyloxy)phenoxy)propanoate;
butyl (R)-2-[4-[5-(trifluoromethyl)-2-pyridinyloxy]-phenoxy]propionate;
ethyl 2-[4-[(6-chloro-2-benzoxazolyl)oxy]phenoxy] propanoate;
butyl 2-[4-[[5-(trifluoromethyl)-2-pyridinyl]oxy]phenoxy] propionate;
2-[4-[(6-chloro-2-quinoxalinyl)oxy]phenoxy]propionic acid, ethyl ester;

URACILS 5-bromo-3-s-butyl-6-methyluracil;
5-bromo-3-cyclohexyl-1,6-dimethyluracil;
3-cyclohexyl-5,6-trimethyleneuracil;
5-bromo-3-isopropyl-6-methyluracil;
3-tert-butyl-5-chloro-6-methyluracil;

NITRILES 2,6-dichlorobenzonitrile;
diphenylacetonitrile;
3,5-dibromo-4-hydroxybenzonitrile;
3,5-diiodo-4-hydroxybenzonitrile;

OTHER ORGANIC HERBICIDES 2-chloro-N,N-diallylacetamide;
N-(1,1-dimethyl-2-propynyl)-3,5-dichlorobenzamide;
maleic hydrazide;
3-amino-1,2,4-triazole; monosodium methanearsonate; disodium methanearsonate;
N,N-dimethyl-alpha,alpha-diphenylacetamide; N-N-di(n-propyl)-2,6-dinitro-4-(trifluoromethyl)aniline; N,N-di(n-propyl)-2,6-dinitro-4-methylaniline; N,N-di(n-propyl)-2,6-dinitro-4-methylsulfonylaniline; O-(2,4-dichlorophenyl)-O-methyl isopropylphosphoramidothioate;
4-amino-3,5,6-trichloropicolinic acid;
2,3-dichloro-1,4-naphthoquinone;
di(methoxythiocarbonyl)disulfide;
3-(1-methylethyl)-1H-2,1,3-benzothiadiazin-(4)3H-one-2,2-dioxide;
6,7-dihydrodipyridol[1,2-a:2',1'-c]pyrazidiium salts;
1,1'-dimethyl-4,4'-bipyridinium salts;
3,4,5,6-tetrahydro-3,5-dimethyl-2-thio-2H-1,3,5-thiadiazine;
2-[1-(ethoxyimino)butyl]-5-[s-(ethylthio)propyl]-3-hydroxy-2-cyclohexen-1-one;
2-(2-chlorophenyl)methyl-4,4-dimethyl-3-isoxazolidinone;
N-(1-ethylpropyl)-3,4-dimethyl-2,6-dinitrobenzamide;
4-chloro-5-(methylamino)-2-(a,a,a-trifluoro-m-toluyl)-3-(2H)-pyridazinone;
2-(3,5-dichlorophenyl)-2-(2,2,2-trichloromethyl)oxirane.

The herbicidal activity and selectivity of a number of example compounds of the present invention towards a variety of common weeds was evaluated using the following test procedure:

Seeds of selected plants were planted in flats or pots. For preemergence tests, immediately after planting the test compound was sprayed directly onto the soil surface. The flats or pots were placed in the greenhouse and then watered. For postemergence tests, the seeds were allowed to germinate and grow for 10 to 21 days prior to application of the test compound. Before application of the test compound, each series of test plants was selected for uniformity, size, and stage of development. The test plants were then treated with the test compound, returned to the greenhouse and watered.

The compound to be evaluated was dissolved in an appropriate solvent, usually acetone, and sprayed over the flats or pots using a carrier volume equivalent to approximately 38 or 77 liters per hectare at the application rate in gram per hectare specified in Table IV. Approximately 2 or 3 weeks after application of the test compound, the growth stage of the plant was determined. Each plant species was evaluated on a scale of 0–100 in which 0 equals no activity and 100 equals total control.

TABLE IV

| Ex. # | Applic. Rate g/Ha | NS | SMT | VEL | BYG | CRB | FOX |
|---|---|---|---|---|---|---|---|
| Greenhouse Testing Results — Teste Weed | | | | | | | |
| Preemergence Tests | | | | | | | |
| 1 | 4800 | — | 0 | 61 | 98 | — | 100 |
| 2 | 4800 | — | 0 | 0 | 71 | — | 81 |
| 22 | 4800 | — | 0 | 21 | 100 | — | 99 |
| 31 | 4800 | — | — | 0 | 0 | — | 0 |
| 42 | 1200 | 0 | 100 | 75 | 95 | 100 | 95 |
| 50 | 2460 | 0 | 0 | 0 | 50 | 98 | 95 |
| Postemergence Tests | | | | | | | |
| 1 | 4800 | — | 5 | 6 | 0 | — | 0 |
| 2 | 4800 | — | 0 | 0 | 0 | — | 0 |
| 22 | 4800 | — | 0 | 0 | 0 | — | 0 |
| 31 | 4800 | — | 0 | 0 | 0 | — | 0 |
| 42 | 1200 | 75 | 0 | 75 | 0 | 70 | 0 |

Tested Weeds:
NS = Nightshade *Solanum nigrum*
SMT = Smartweed *Polygonum lapathifolium*
VEL = Velvetleaf *Abutilon theophrasti*
BYG = Barnyardgrass *Echinochloa crus-galli*
CRB = Crabgrass *Digitaria sanguinalis*
FOX = Green Foxtail *Setaria viridis*

We claim:

1. A method of controlling unwanted vegetation comprising contacting the unwanted vegetation with an herbicidally effective amount of a compound of the formula:

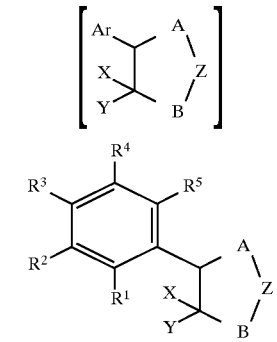

wherein:

$R^1$, $R^2$, $R^3$, $R^4$, and $R^5$ are independently H, alkoxy, nitro, halo, or alkyl;

A and B are each $CH_2$;

Z is CH=CH, $CH_2$—$CH_2$, or CMe=CMe;

X and Y are independently H, $NO_2$, CN, halogen, or $CH_2NO_2$, provided that X and Y are not both H;

its diastereomers and stereoisomers.

2. The method of claim 1 wherein two or three of $R^1$, $R^2$, $R^3$, $R^4$, and $R^5$ are H and the others of $R^1$, $R^2$, $R^3$, $R^4$, and $R^5$ are halo, ($C_1$–$C_4$)alkyl, ($C_1$–$C_4$)alkoxy; one of X and Y is H or halo and the other of X and Y is $NO_2$ or CN; and Z is $CH_2$—$CH_2$ or CH=CH.

3. The method of claim 1 wherein $R^1$ and $R^5$ are H and $R^2$, $R^3$, and $R^4$ are independently ($C_1$–$C_4$)alkyl, ($C_1$–$C_4$)alkoxy, or halo one of X and Y is H and the other of X and Y is $NO_2$ or CN, and Z is $CH_2$—$CH_2$ or CH=CH.

4. The method of claim 1 wherein the compound is applied to the unwanted vegetation, to the locus of the unwanted vegetation, or to the growth medium of the unwanted vegetation at an application rate of from from 0.01 Kg. to 10 Kg. per hectare.

5. The method of claim 4 wherein the application rate is from 0.1 Kg. to 4 Kg. per hectare.

6. An herbicidal composition comprising the compound of claim 1 and an agronomically acceptable carrier.

7. The herbicidal composition of claim 6 comprising the compound of claim 1 wherein $R^1$ and $R^5$ are H and $R^2$, $R^3$, and $R^4$ are independently $(C_1-C_4)$alkyl, $(C_1-C_4)$alkoxy, or halo, A and B are each $CH_2$, one of X and Y is H and the other of X and Y is $NO_2$ or CN, and Z is CH=CH.

8. The herbicidal composition of claim 6 wherein the compound comprises from 0.01 to 99.9 percent by weight of the composition.

9. The herbicidal composition of claim 6 wherein the compound comprises from 1.0 to 85 percent by weight of the composition.

10. The composition of claim 6 further comprising a fertilizer.

11. The composition of claim 10 wherein the compound comprises from 5 to 25 percent by weight of the composition.

* * * * *

UNITED STATES PATENT AND TRADEMARK OFFICE
CERTIFICATE OF CORRECTION

PATENT NO.     : 5,866,513              Page 1 of 1
DATED          : February 2, 1999
INVENTOR(S)    : Enrique Luis Michelotti et al.

It is certified that error appears in the above-identified patent and that said Letters Patent is hereby corrected as shown below:

Column 26,
Line 53, replace "X and Y are independently II, NO$_2$, CN, halogen, or" with
-- X and Y are independently H, NO$_2$, CN, halogen, or --

Signed and Sealed this

Seventeenth Day of December, 2002

JAMES E. ROGAN
*Director of the United States Patent and Trademark Office*